United States Patent
Wilk

(10) Patent No.: US 7,753,934 B2
(45) Date of Patent: Jul. 13, 2010

(54) MEDICAL CLOSURE METHOD AND ASSOCIATED DEVICE

(75) Inventor: Peter J. Wilk, New York, NY (US)

(73) Assignee: Wilk Patent, LLC, New York, NY (US)

( * ) Notice: Subject to any disclaimer, the term of this patent is extended or adjusted under 35 U.S.C. 154(b) by 1147 days.

(21) Appl. No.: 11/387,528

(22) Filed: Mar. 23, 2006

(65) Prior Publication Data
US 2006/0241688 A1   Oct. 26, 2006

Related U.S. Application Data

(60) Provisional application No. 60/674,387, filed on Apr. 22, 2005.

(51) Int. Cl.
*A61B 17/00* (2006.01)
(52) U.S. Cl. ...................................................... 606/213
(58) Field of Classification Search ................ 606/213, 606/215, 151, 157, 158; 128/898
See application file for complete search history.

(56) References Cited

U.S. PATENT DOCUMENTS

| | | | |
|---|---|---|---|
| 4,852,568 A | 8/1989 | Kensey | |
| 5,297,536 A | 3/1994 | Wilk | |
| 5,458,131 A | 10/1995 | Wilk | |
| 5,810,721 A | 9/1998 | Mueller | |
| 5,948,427 A | 9/1999 | Yamamoto | |
| 6,126,675 A * | 10/2000 | Shchervinsky et al. | 606/213 |
| 6,171,329 B1 * | 1/2001 | Shaw et al. | 606/213 |
| 6,245,076 B1 | 6/2001 | Yan | |

* cited by examiner

*Primary Examiner*—Kevin T Truong
(74) *Attorney, Agent, or Firm*—R Neil Sudol; Henry D. Coleman; William J. Sapone

(57) ABSTRACT

A surgical closure method utilizes a surgical device including an elongate tube, a flexible web member disposed in a collapsed configuration inside the tube, and a push rod disposed at least partially inside the tube for pushing the web member from the tube. A distal end portion of the tube is inserted through an opening or wound in a wall of a hollow body organ. The rod is pushed in a distal direction along the tube to eject the web member from the distal end of the tube. The ejected web member is expanded from the collapsed configuration to an expanded configuration. The expanded web member is placed in contact with the wall of the organ over the opening or wound. Subsequently the expanded web member is attached to the wall of the organ.

15 Claims, 4 Drawing Sheets

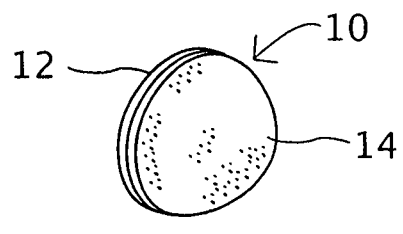
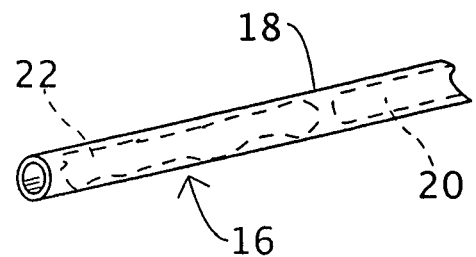
FIG. 1  FIG. 2
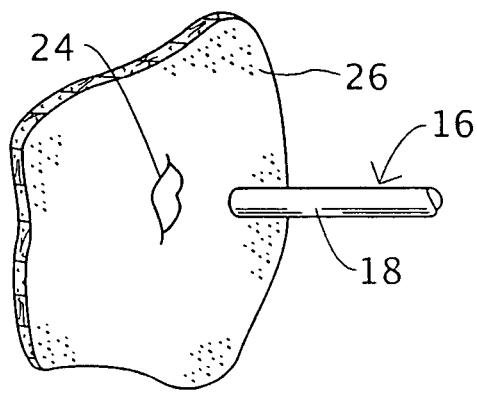
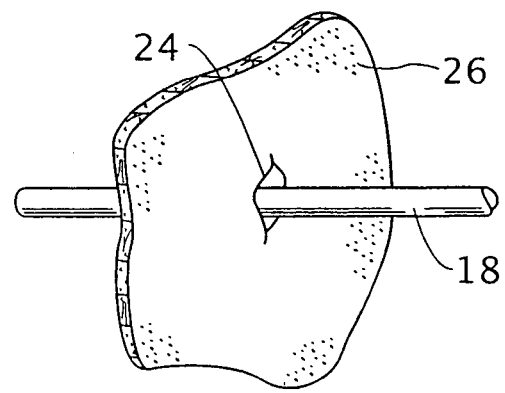
FIG. 3A  FIG. 3B

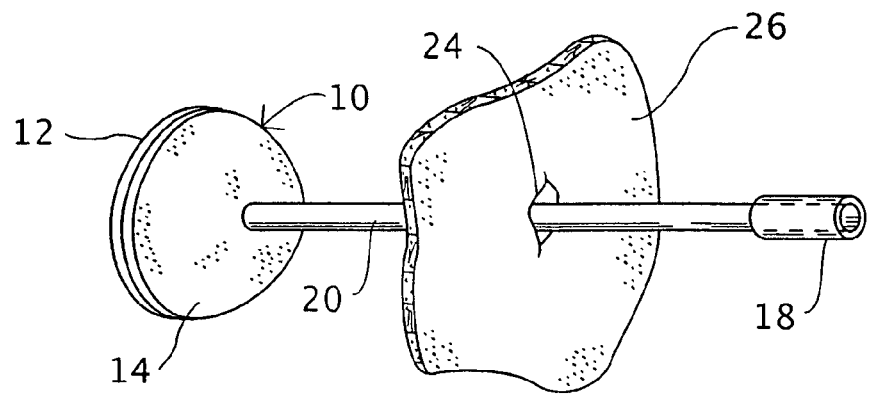
FIG. 3C
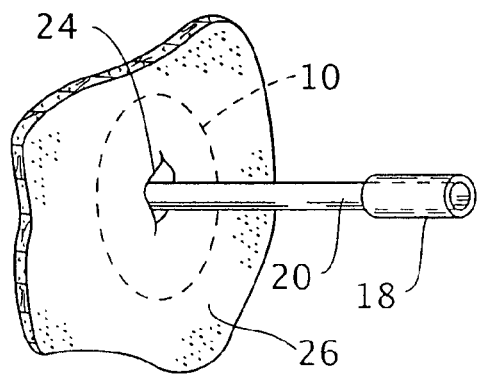 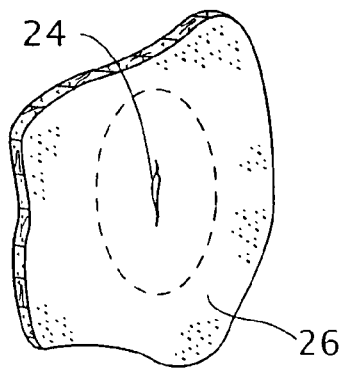
FIG. 3D     FIG. 3E

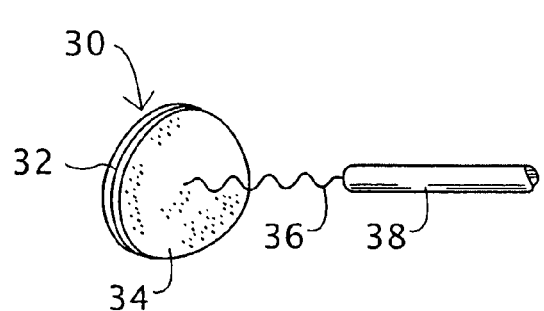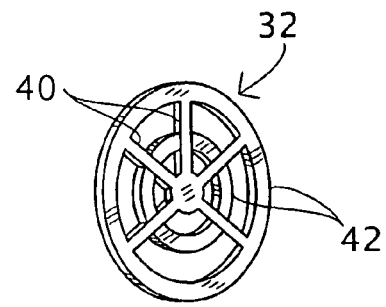
FIG. 4     FIG. 5
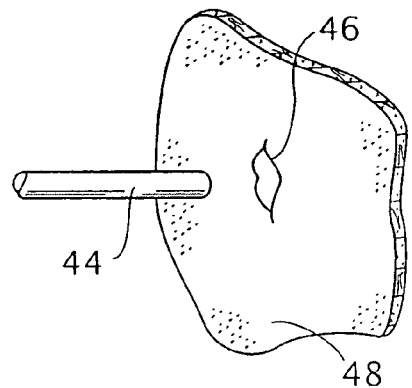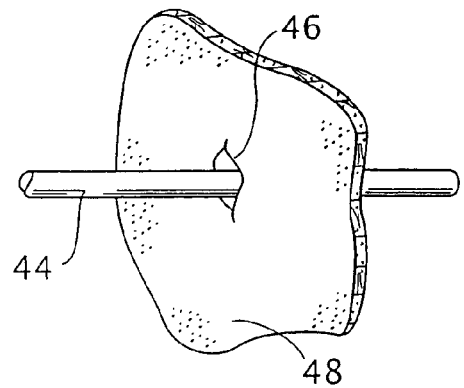
FIG. 6A     FIG. 6B

MEDICAL CLOSURE METHOD AND ASSOCIATED DEVICE

CROSS-REFERENCE TO RELATED APPLICATION

This application claims the benefit of U.S. Provisional Patent Application No. 60/674,387 filed Apr. 22, 2005.

BACKGROUND OF THE INVENTION

This invention relates to a method and an associated device for closing openings such as wounds and incisions in walls of hollow internal organs. The present invention is particularly, but not exclusively, useful in medical procedures carried out without the formation of an incision in a skin surface of the patient.

Such procedures are described in U.S. Pat. Nos. 5,297,536 and 5,458,131.

As described in those patents, a method for use in intra-abdominal surgery comprises the steps of (a) inserting an incising instrument with an elongate shaft through a natural body opening into a natural body cavity of a patient, (b) manipulating the incising instrument from outside the patient to form a perforation in an internal wall of the natural internal body cavity, and (c) inserting a distal end of an elongate surgical instrument through the natural body opening, the natural body cavity and the perforation into an abdominal cavity of the patient upon formation of the perforation. Further steps of the method include (d) inserting a distal end of an endoscope into the abdominal cavity, (e) operating the surgical instrument to perform a surgical operation on an organ in the abdominal cavity, (f) viewing the surgical operation via the endoscope, (g) withdrawing the surgical instrument and the endoscope from the abdominal cavity upon completion of the surgical operation, and (h) closing the perforation.

Visual feedback may be obtained as to position of a distal end of the incising instrument prior to the manipulating thereof to form the perforation. That visual feedback may be obtained via the endoscope or, alternatively, via radiographic or X-ray equipment.

The abdominal cavity may be insufflated prior to the insertion of the distal end of the endoscope into the abdominal cavity. Insufflation may be implemented via a Veress needle inserted through the abdominal wall or through another perforation in the internal wall of the natural body cavity. That other perforation is formed by the Veress needle itself. U.S. Pat. No. 5,209,721 discloses a Veress needle that utilizes ultrasound to detect the presence of an organ along an inner surface of the abdominal wall.

A method in accordance with the disclosures of U.S. Pat. Nos. 5,297,536 and 5,458,131 comprises the steps of (i) inserting an endoscope through a natural body opening into a natural body cavity of a patient, (ii) inserting an endoscopic type incising instrument through the natural body opening into the natural body cavity, (iii) manipulating the incising instrument from outside the patient to form a perforation in an internal wall of the natural internal body cavity, (iv) moving a distal end of the endoscope through the perforation, (v) using the endoscope to visually inspect internal body tissues in an abdominal cavity of the patient, (vi) inserting a distal end of an elongate surgical instrument into the abdominal cavity of the patient, (vii) executing a surgical operation on the internal body tissues by manipulating the surgical instrument from outside the patient, (viii) upon completion of the surgical operation, withdrawing the surgical instrument and the endoscope from the abdominal cavity, (ix) closing the perforation, and (x) withdrawing the endoscope from the natural body cavity.

The trans-organ surgical procedures of U.S. Pat. Nos. 5,297,536 and 5,458,131 reduce trauma to the individual even more than laparoscopic procedures. Hospital convalescence stays are even shorter. There are some potential problems with performing a trans-organ surgical procedure, such as the difficulty in forming, at the end of the procedure, an effectively fluid tight closure of the perforation formed in the wall of the hollow internal body organ. Certain intra-abdominal operations cannot be easily performed owing to the necessity of removing large chunks of organic or inorganic material (e.g., entire kidney, myoma from uterus). Some operations can require the simultaneous usage of many different instruments so that space along the selected pathways may be difficult to find.

OBJECTS OF THE INVENTION

It is an object of the present invention to provide improvements on the afore-described surgical procedures.

It is another object of the present invention to provide a surgical closure method and/or associated surgical device that is particularly useful in closing perforations or incisions formed in the walls of hollow internal body organs during trans-organ surgery.

A further object of the present invention is to provide a method and/or an associated device for use in rigid laparoscopy and/or flexible trans-organ surgery.

These and other objects of the present invention will be apparent from the drawings and detailed descriptions herein. While every object of the invention is believed to be attained in at least one embodiment of the invention, there is not necessarily any single embodiment that achieves all of the objects of the invention.

SUMMARY OF THE INVENTION

A surgical device in accordance with the present invention comprises an elongate tube, a flexible web member disposed in a collapsed configuration inside the tube, and a push rod disposed at least partially inside the tube for pushing the web member from the tube. Preferably, but not necessarily, the web member has a substantially disk-shaped expanded configuration. Because the web member is flexible, it is conformable to the surfaces of organs of different shapes.

Pursuant to another feature of the present invention, the web member incorporates means for expanding the web member from the collapsed configuration to the expanded configuration. This means may include a shape-memory material incorporated into or connected to at least a portion of the web member. The shape-memory material may be Nitinol and take the form of a ring and/or ribs. The ribs may be arranged in a network or lattice such as radiating spokes of a wheel.

Pursuant to a further feature of the present invention, the web member is provided along a major surface with a layer of an adhesive substance. Preferably, the layer of adhesive is deposited on the major surface of the web member at the time of manufacture. Concomitantly, the adhesive substance is preferably in an inactive, dormant or non-adhesive state until the application of a predetermined form of activation energy. This enables the disposition of the web member in a closed configuration inside the tube prior to deployment during a surgical procedure.

Pursuant to additional features of the present invention, the rod is connected to the web member and extends from the major surface of the web member.

A surgical closure method in accordance with the present invention utilizes a surgical device including an elongate tube, a flexible web member disposed in a collapsed configuration inside the tube, and a push rod disposed at least partially inside the tube for pushing the web member from the tube. The method comprises inserting a distal end portion of the tube through an opening or wound in a wall of a hollow body organ, pushing the rod in a distal direction along the tube, consequently ejecting the web member from the distal end of the tube, expanding the ejected web member from the collapsed configuration to an expanded configuration, placing the expanded web member in contact with the wall of the organ over the opening or wound, and subsequently attaching the expanded web member to the wall of the organ.

According to another aspect of the present invention, the attaching of the expanded web member to the wall of the organ includes adhesively attaching the expanded web member to the wall. The adhesive may be applied to a major surface of the web member after the unfolding or expanding thereof inside a patient (for instance, inside an abdominal cavity that is insufflated with carbon dioxide gas). A tube with a spray nozzle may be inserted into the patient for coating the major surface of the web member with a layer of the adhesive. Alternatively and preferably, the adhesive is applied to a major surface of the web member at the time of manufacture. In that case, the adhesive layer on the web member is in an inactive or dormant state. After the expanding of the web member and before or after the bringing of the coated major surface of the web member into contact with the organ wall around the opening or wound in the hollow internal organ, a predetermined form of activation energy is applied to the layer of adhesive material to activate the adhesive material. The activation energy may take any suitable form including heat energy, infrared radiation and ultrasonic pressure waves. If the activation energy is applied prior to the bringing of the web member into contact with the organ wall, the activation energy may be applied to the adhesive layer via an instrument having a distal end portion inserted through the opening or wound in the organ wall. If the activation energy is applied after the bringing of the web member into contact with the organ wall, the activation energy may be applied to the adhesive layer through the organ wall. In this case, however, it is possible that the activation energy is applied through the web member, from inside the patient.

The method of the present invention is useful for closing perforations formed in the abdominal wall during laparoscopic procedures. The method of the present invention is particularly useful for closing perforations formed in internal organs during trans-organ surgery as described in U.S. Pat. Nos. 5,297,536 and 5,458,131. The distal end portion of the surgical closure device is inserted through a natural body opening such as the mouth, the vaginal orifice, the anus, or the urinary bladder and utilized as discussed above to close a perforation formed in the wall of the stomach, the vagina, the colon, or the urinary bladder, respectively. This method is effective in part because the web member is attached to the outer side of the organ, rather than the inner side. The inner side of the organ is typically formed by a mucosal membrane, to which it is difficult to form any sort of attachment.

As indicated above, the web member may be attached to the rod, either directly or via another tensile element such as a string. In that case, the placing the expanded web member in contact with the organ wall including pulling the rod (and tensile element, if any) in a proximal direction to move the web member into contact with the wall. One continues to apply tension on the rod for an interval sufficient to ensure a secured attachment of the web member to the organ wall. Thereafter, the rod is detached from the web member, for instance, by cutting the rod (or tensile element).

Pursuant to a further aspect of the present invention, the expanding of the web member from the collapsed configuration is achieved automatically by virtue of a shape-memory material incorporated into or attached to at least a portion of the web member.

BRIEF DESCRIPTION OF THE DRAWING

FIG. 1 is a schematic perspective view of a surgical patch in an expanded use configuration, in accordance with the present invention.

FIG. 2 is a schematic perspective view of a surgical closure instrument in accordance with the present invention, showing the patch of FIG. 1 in a folded or collapsed configuration inside a distal end of a delivery tube, distally of an ejection rod.

FIGS. 3A-3E are a series of schematic perspective views depicting successive steps in a surgical closure procedure utilizing the instrument of FIG. 2.

FIG. 4 is a schematic perspective view showing the application of activation energy to a layer of inactive or dormant adhesive on a disk-shaped surgical patch in accordance with another embodiment of the present invention.

FIG. 5 is an elevational view of a disk-shaped patch in accordance with the present invention, showing elements on the patch for inducing the patch to open from a closed storage configuration to an opened use configuration.

FIGS. 6A-6F are a series of schematic perspective views depicting successive steps in a surgical closure procedure utilizing the instrument of FIG. 2 including a patch provided with a layer of inactive or dormant adhesive material.

DETAILED DESCRIPTION

Figures 6C, 6D:
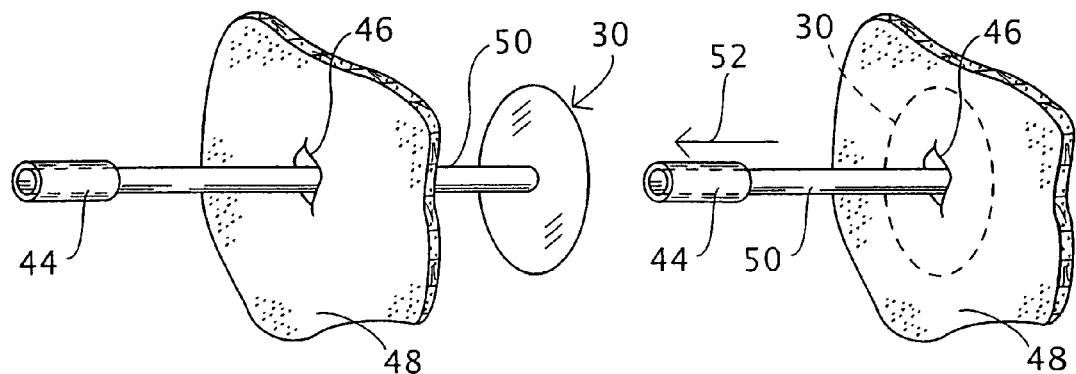

As illustrated in FIG. 1, a surgical closure patch 10 comprises a disk-shaped web member 12 provided with a layer of adhesive material 14. The layer of adhesive material 14 is deposited on the web member 12 at the time of manufacture. As illustrated in FIG. 2, a surgical closure device 16 comprises a delivery tube 18 and an ejection rod 20 inserted in the delivery tube. Patch 10 is provided in a folded or collapsed configuration 22 inside a distal end of delivery tube 18.

Closure device 16 is used exemplarily during a laparoscopic procedure to close a perforation in the abdominal wall or in an internal organ of a patient. The method of the present invention is particularly useful for closing perforations formed in internal organs during trans-organ surgery as described in U.S. Pat. Nos. 5,297,536 and 5,458,131. The distal end portion of surgical closure device 10 particularly including delivery tube 18 is inserted through a natural body opening such as the mouth, the vaginal orifice, the anus, or the urethral opening and utilized as discussed below with reference to FIGS. 3A-3E or 6A-6F to close a perforation formed in the wall of the stomach, the vagina, the colon, or the urinary bladder, respectively. To that end, delivery tube 18 and rod 20 are flexible members that enable the insertion of device 16 along a path having one or more curves.

During trans-organ surgery as described in U.S. Pat. Nos. 5,297,536 and 5,458,131, a perforation, opening, wound, or incision 24 is formed in a wall 26 of an internal hollow body organ. At the end of the procedure, perforation or incision 24 is closed by inserting a distal end portion (not separately enumerated) of the device 16, particularly including tube 18, into the hollow body organ through a natural orifice, as shown in FIG. 3A. The distal end portion of device 16 is then inserted through perforation 24, as shown in FIG. 3B. Subsequently, ejection or push rod 20 is shifted in the distal direction along tube 18 to eject web member 12 from the distal end of the tube. Then, the ejected web member 12 expands from the collapsed configuration 22 to the expanded configuration, as shown in FIG. 3C. The expanded surgical patch 10 is placed in contact with the wall 26 of the organ over the perforation 24 by pulling rod 20 in the proximal direction as indicated by an arrow 28 in FIG. 3D. Upon the formation of an adhesive bond between layer 14 of patch 10 and an outer surface of organ wall 26, attaching the expanded web member 12 to the organ wall, rod 20 is detached from web member 12, thereby leaving patch 10 in place over the perforation 24. This detachment may be implemented, for instance, by twisting rod 20 about its longitudinal axis. To that end, rod 20 may be provided with a score line (not shown) at a distal end, in the vicinity of web member 12, to facilitate the separation of rod 20 from web member 12. Of course, after the separation of rod 20 from web member 12, rod 20 and delivery tube 18 are removed from the patient via the natural body opening through which they were inserted.

Web member 12 and rod 20, at least at the distal end thereof, are made of a biocompatible and optionally bioabsorbable material. The adhesive material of layer 14 is also biocompatible and optionally bioabsorbable.

In the embodiment of FIGS. 2 and 3A-3E, adhesive layer 14 may be rendered temporarily inactive through the application of a protective lubricating film of a volatile substance that dissipates into the insufflated abdominal cavity (see U.S. Pat. Nos. 5,297,536 and 5,458,131), thereby rendering adhesive layer 14 active.

As illustrated in FIG. 4, a surgical patch 30 has a disk-shaped web member 32 made of a flexible biocompatible material and a layer of adhesive material 34 that is applied to web member 32 in a dormant or inactive state. The adhesive material is rendered active (e.g., tacky) by applying energy 36 to the adhesive layer 34 via an instrument or device 38. The energy 36 may by heat energy, infrared radiation, ultrasonic pressure wave energy, etc.

As depicted in FIG. 5, web member 32 is provided with a shape-memory network or lattice extending between a center of the web member and a periphery thereof and including a series of radiating ribs 40 and rings 42 made of a shape-memory material such as Nitinol. Upon ejection of web member 32 from a delivery tube 44 (FIG. 6A), the web member expands from a collapsed configuration into an expanded configuration under forces exerted by the shape-memory material of ribs 40 and rings 42.

During trans-organ surgery as described in U.S. Pat. Nos. 5,297,536 and 5,458,131, a perforation, opening, wound, or incision 46 is formed in a wall 48 of an internal hollow body organ. At the end of the procedure, perforation or incision 46 is closed by inserting a distal end portion (not separately enumerated) of delivery tube 44 into the hollow body organ through a natural orifice, as shown in FIG. 6A. The distal end portion of tube 44 is then inserted through perforation 46, as shown in FIG. 6B. Subsequently, an ejection or push rod 50 is shifted in the distal direction along tube 44 to eject web member 32 from the distal end of the tube. Then, the ejected web member 32 expands from the collapsed configuration, as shown in FIG. 6C. The expanded surgical patch 30 is placed in contact with the wall 48 of the organ over the perforation 46 by pulling rod 50 in the proximal direction as indicated by an arrow 52 in FIG. 6D.

Delivery tube 44 is generally pulled back through incision or perforation 46 prior to the pulling of the expanded patch 30 in contact with the outer (non-mucosal) surface of organ wall 48. Thereafter a distal end portion of instrument 38 is inserted into the patient, exemplarily via the same path as delivery tube 44, and the instrument is operated to apply activation energy 36 to adhesive layer 34 through organ wall 48 to thereby activate the adhesive material (FIG. 6E).

Figures 6E, 6F:
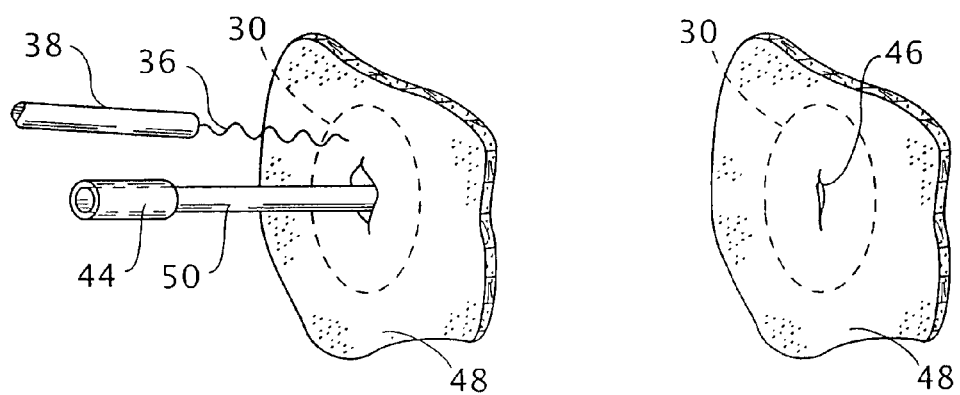

Upon the formation of an adhesive bond between layer 34 of patch 30 and an outer surface of organ wall 48, attaching the expanded web member 32 to the organ wall, rod 50 is detached from web member 32, thereby leaving patch 30 in place over the perforation 46 only on the outer surface of organ wall 48, with an inner side of organ wall 48 being free of the closure device, as depicted in FIG. 6F. This detachment may be implemented as discussed above, by twisting rod 50 about its longitudinal axis. To that end, rod 50 may be provided with a score line (not shown) at a distal end, in the vicinity of web member 32, to facilitate the separation of rod 50 from web member 32. Of course, after the separation of rod 50 from web member 32, rod 50 and delivery tube 44 are removed from the patient via the natural body opening through which they were inserted.

Although the invention has been described in terms of particular embodiments and applications, one of ordinary skill in the art, in light of this teaching, can generate additional embodiments and modifications without departing from the spirit of or exceeding the scope of the claimed invention. For instance, adhesive layer 14 may be applied to a major surface of web member 12 after the unfolding or expanding thereof inside a patient (for instance, inside an abdominal cavity that is insufflated with carbon dioxide gas). A tube with a spray nozzle (not shown) may be inserted into the patient for coating the major surface of the web member with the layer of adhesive.

In another alternative procedure, activation energy 36 may be applied to adhesive layer 34 after the expansion of web member 32 from the collapse configuration and prior to the bringing of the expanded web member into contact with organ wall 48. In that case, activation energy 36 is applied to adhesive layer 34 via instrument 38 by first inserting a distal end portion of that instrument through the perforation 46 in organ wall 48. Activation energy 36 is then applied directly to adhesive layer 34 inside the abdominal cavity of the patient.

Generally, activation energy 36 can take the form of electromagnetic radiation of any suitable frequency band. Alternatively, ultrasonic vibrational energy may be the activating energy 36.

In a further alternative procedure, activation energy 36 is applied through web member 32, for instance, from inside the abdominal cavity of the patient. In that case, the distal end portion of instrument 38 is inserted into the patient along an alternate route different from the path of tube 44 and rod 50.

Instrument 38 may be inserted into the patient via tube 44. Alternatively, the functions of instrument 38 may be incorporated as an integral part of tube 44.

Accordingly, it is to be understood that the drawings and descriptions herein are proffered by way of example to facilitate comprehension of the invention and should not be construed to limit the scope thereof.

What is claimed is:

1. A surgical device comprising:
   an elongate tube;
   a flexible web member disposed in a collapsed configuration inside said tube, said web member having an expanded configuration substantially in the form of a disk; and a push rod disposed at least partially inside said tube for pushing said web member from said tub, said web member being provided with a shape-memory network or lattice extending between a center of said web member and a periphery thereof for expanding said web member from said collapsed configuration to a predetermined expanded configuration upon an ejection of said web member from said tube by action of said push rod.

2. The surgical device defined in claim 1 wherein said web member is provided along a major surface with a layer of an adhesive substance.

3. The surgical device defined in claim 2 wherein said adhesive substance is in an inactive or non-adhesive state until the application of a predetermined form of activation energy.

4. The surgical device defined in claim 2 wherein said rod is connected to said web member and extends from said major surface of said web member.

5. The surgical device defined in claim 1 wherein said rod is connected to said web member and extends from a major surface of said web member.

6. The surgical device defined in claim 1 wherein said network or lattice includes radially oriented components and ring-shaped components.

7. A surgical closure method comprising:

providing a surgical device including an elongate tube, a flexible web member disposed in a collapsed configuration inside said tube, and a push rod disposed at least partially inside said tube for pushing said web member from said tube;

passing a distal end portion of said tube through a natural body orifice into a hollow body organ of a patient;

inserting said distal end portion of said tube through an opening or wound in a wall of said hollow body organ;

pushing said rod in a distal direction along said tube;

by virtue of the pushing of said rod, ejecting said web member from the distal end of said tube;

expanding the ejected web member from said collapsed configuration to an expanded configuration;

placing the expanded web member in contact with said wall of said organ over said opening or wound; and subsequently attaching the expanded web member to said wall of said organ.

8. The method defined in claim 7 wherein the attaching of said expanded web member to said wall of said organ includes adhesively attaching said expanded web member to said wall.

9. The method defined in claim 8 wherein said web member is provided along a major surface with a layer of dormant or inactive adhesive material, placing the expanded web member in contact with said wall including placing said major surface with said layer of adhesive material in contact with said wall, the attaching of said expanded web member to said wall further including applying a predetermined form of activation energy to said layer of adhesive material to activate said adhesive material.

10. The method defined in claim 7 wherein the web member is attached to said rod inside said tube, the placing the expanded web member in contact with said wall including pulling said rod in a proximal direction to move said web member into contact with said wall.

11. The method defined in claim 10 wherein said web member is part of a medical closure device sealing said opening or wound, further comprising detaching said rod from said web member after the attaching of the expanded web member to said wall; removing said tube and said rod from said hollow body organ; and maintaining said expanded web member in the patient so that said closure member is substantially located only on an outer side of said wall, away from said natural body orifice, and so that an inner side of said wall is free or empty of said closure member.

12. The method defined in claim 7 wherein the expanding of said web member from said collapsed configuration is achieved automatically by virtue of a shape-memory material incorporated into or attached to at least a portion of said web member.

13. A surgical closure method comprising:

providing a surgical device including an elongate tube, a closure member in the form of a flexible web member disposed in a collapsed configuration inside said tube, and a push rod disposed at least partially inside said tube for pushing said web member from said tube;

inserting a distal end portion of said tube through an opening or wound in a wall of a hollow body organ, from an inner side of said wall to an outer side thereof;

pushing said rod in a distal direction along said tube;

by virtue of the pushing of said rod, ejecting said web member from the distal end of said tube;

expanding the ejected web member from said collapsed configuration to an expanded configuration;

placing the expanded web member in contact with said outer said of said wall of said organ over said opening or wound; and subsequently attaching the expanded web member to said outer side of said wall of said organ so that inner side of said wall is free of said closure member and said closure member is substantially disposed only along said outer side of said wall.

14. The method defined in claim 13 wherein the web member is attached to said rod inside said tube, the placing the expanded web member in contact with said outer side of said wall including pulling said rod in a proximal direction to move said web member into contact with said outer side of said wall.

15. The method defined in claim 14, further comprising detaching said rod from said web member after the attaching of the expanded web member to said wall.

* * * * *